(12) United States Patent
Bodart

(10) Patent No.: US 6,878,840 B2
(45) Date of Patent: *Apr. 12, 2005

(54) PROCESS FOR POLYMERIZATION OF VINYL CHLORIDE

(75) Inventor: Vincent Bodart, Namur (BE)

(73) Assignee: Solvay (Societe Anonyme), Brussels (BE)

(*) Notice: Subject to any disclaimer, the term of this patent is extended or adjusted under 35 U.S.C. 154(b) by 0 days.

This patent is subject to a terminal disclaimer.

(21) Appl. No.: 10/658,314

(22) Filed: Sep. 8, 2003

(65) Prior Publication Data

US 2004/0048995 A1 Mar. 11, 2004

Related U.S. Application Data

(60) Continuation of application No. 09/866,026, filed on May 25, 2001, now Pat. No. 6,617,408, which is a division of application No. 09/117,098, filed as application No. PCT/EP97/00164 on Jan. 10, 1997, now Pat. No. 6,258,906.

(30) Foreign Application Priority Data

Jan. 26, 1996 (BE) .......................................... 96000707

(51) Int. Cl.⁷ .............................................. C08C 69/96
(52) U.S. Cl. ..................................... 558/264; 558/280
(58) Field of Search ................................ 558/264, 280; 526/227

(56) References Cited

U.S. PATENT DOCUMENTS

| | | | |
|---|---|---|---|
| 2,370,588 A | * | 2/1945 | Strain .......................... 558/264 |
| 3,377,373 A | | 4/1968 | Lederer et al. |
| 3,575,945 A | | 4/1971 | Cantoni et al. |
| 3,799,916 A | | 3/1974 | Langsam |
| 3,849,468 A | | 11/1974 | Busseret |
| 3,933,776 A | | 1/1976 | Fournel et al. |
| 3,935,243 A | | 1/1976 | Priddy |
| 3,950,375 A | | 4/1976 | McKee et al. |
| 4,260,541 A | | 4/1981 | Kolinsky et al. |
| 4,495,312 A | | 1/1985 | Hata et al. |
| 4,584,142 A | | 4/1986 | Tang et al. |
| 4,590,008 A | | 5/1986 | Tang et al. |
| 5,548,046 A | | 8/1996 | Sanchez |
| 6,255,520 B1 | * | 7/2001 | Lannuzel et al. ........... 558/264 |
| 6,258,906 B1 | * | 7/2001 | Bodart ....................... 526/227 |
| 6,617,408 B2 | * | 9/2003 | Bodart ..................... 526/230.5 |
| 6,627,717 B2 | * | 9/2003 | Lannuzel et al. ......... 526/230.5 |

FOREIGN PATENT DOCUMENTS

| | | |
|---|---|---|
| DD | 118 608 | 4/1975 |
| GB | 1 107 956 | 3/1968 |
| GB | 1 484 675 | 9/1977 |
| GB | 2 022 104 | 12/1979 |
| GB | 2 024 224 | 1/1980 |
| GB | 1 583 481 | 1/1981 |
| HU | 209730 | 10/1994 |
| JP | 56183848 | 5/1983 |
| LU | 44879 | 11/1963 |

OTHER PUBLICATIONS

CRC Handbook of Chemistry and Physics, 59th ed. (1978–1979) pp. D–265, D–299 and D–300.

Plastic Additives Handbook, 4th ed. (1993) pp. 382–385 and 403.

* cited by examiner

Primary Examiner—Tatyana Zalukaeva
(74) Attorney, Agent, or Firm—Morrison & Foerster LLP

(57) ABSTRACT

The dialkyl peroxydicarbonates with short alkyl chains, preferably diethyl and diisopropyl peroxydicarbonates, are used for the aqueous suspension polymerization of vinyl chloride, in the form of a solution in a dialkyl alkanedicarboxylate which is liquid and insoluble in water. The preferred solvents are hexanedicarboxylates (adipates) derived from adipic acid and from $C_6$–$C_{10}$ alkanols. The peroxydicarbonate concentration of the said solutions is generally 15–40% by weight. The process according to the invention produces vinyl chloride polymers of improved quality resulting in shaped articles exhibiting markedly fewer fisheyes.

The invention also relates to a two-stage process for the manufacture of a solution of dialkyl peroxydicarbonates with short alkyl chains which is particularly suited for the aqueous suspension polymerization of vinyl chloride. According to this process an inorganic salt is used in the stage of manufacture of the peroxydicarbonate (first stage) and the latter is subsequently isolated by extraction by means of a water-insoluble solvent (second stage).

19 Claims, No Drawings

PROCESS FOR POLYMERIZATION OF VINYL CHLORIDE

CROSS REFERENCE TO RELATED APPLICATIONS

This application is a continuation of U.S. Ser. No. 09/866,026, filed 25 May 2001, to be issued as U.S. Pat. No. 6,617,408 on Sep. 9, 2003, which is a divisional of U.S. Ser. No. 09/117,098 filed 23 Apr. 1999, now U.S. Pat. No. 6,258,906 issued 10 Jul. 2001, which is the National Phase of PCT Application PCT/EP97/00164 filed 10 Jan. 1997 which claims priority from Belgium Application 96/000707 filed 26 Jan. 1996, each of which is incorporated herein in its entirety.

The present invention relates to a process for the aqueous suspension polymerization of vinyl chloride with the use of dialkyl peroxydicarbonates. It relates more particularly to such a process in which dialkyl peroxydicarbonates with short alkyl chains are used in the form of a solution. The invention also relates to a process for the manufacture of a solution of dialkyl peroxydicarbonate with short alkyl chains.

It is known to make use of dialkyl peroxydicarbonates for initiating the aqueous suspension polymerization of vinyl chloride. Dialkyl peroxydicarbonates with short alkyl chains, such as diethyl and diisopropyl peroxydicarbonates, constitute initiators that are particularly appreciated because of their high activity at the usual temperatures of polymerization of vinyl chloride. However, they have the disadvantage of being unstable, with the result that their storage in the pure state presents very serious hazards.

With a view to overcoming this disadvantage it has already been proposed to manufacture these peroxydicarbonates in the polymerization reactor ("in situ"), for example by reacting alkyl haloformate dissolved in vinyl chloride with a peroxy compound such as hydrogen peroxide, dissolved in alkaline water. This process for "in situ" manufacture of the initiator does not allow an automation of the initiator feed to the polymerization reactors. In addition, it lacks reproducibility (lack of accuracy concerning the quantities of initiator actually introduced into the polymerization) and of production efficiency (need to precede each polymerization cycle with the "in situ", synthesis of the initiator).

It has also been proposed to prepare the quantity of dialkyl peroxydicarbonate which is precisely needed, outside the polymerization reactor ("ex situ") and immediately before the polymerization.

This preparation is performed by reacting an alkyl haloformate with a peroxy compound in the presence of water and of a water-immiscible volatile solvent which preferably has a boiling temperature lower than 100° C., such as pentane or hexane. The initiator solution thus obtained is then introduced in toto (organic phase and aqueous phase) into the polymerization reactor which is subsequently charged with a view to the polymerization (British Patent 1 484 675 in the name of Solvay & Cie). This process allows the initiator feed to the reactors to be automated but still makes it necessary to produce the sufficient precise quantity of initiator immediately before the polymerization. Besides, it does not allow (either) a delayed introduction of the dialkyl peroxydicarbonates, a technique that is advantageous, for example, in order to improve the polymerization kinetics. In addition, just like the above-mentioned process for "in situ" manufacture, it produces vinyl chloride polymers which, after conversion, result in finished articles containing many "fisheyes".

British Patent Application 2 022 104 and French Patent Application 2 352 839 mention processes for the aqueous suspension polymerization of vinyl chloride with the use of dialkyl peroxydicarbonates with short alkyl chains in the presence of respectively a plasticizer or a diacid higher alcohol ester. The processes described in these documents do however not allow to solve the problems linked with the dialkyl peroxydicarbonate instability during storage, the automated initiator feed to the polymerization reactors and the delayed introduction in the polymerization reactor of these initiators.

The U.S. Pat. No. 3,950,375 relates to a continuous process for the manufacture of pure dialkyl peroxydicarbonates by centrifuging the aqueous reaction phase.

The U.S. Pat. No. 3,377,373 describes a continuous process for the manufacture of a diisopropyl peroxydicarbonate solution in carbon tetrachloride.

The aim of the present invention is to provide a process for the aqueous suspension polymerization of vinyl chloride with the use of dialkyl peroxydicarbonates with short alkyl chains which does not exhibit any of the abovementioned disadvantages. It also aims to provide an improved process for the manufacture of a solution of dialkyl peroxydicarbonates which are particularly suited for use in the aqueous suspension polymerization of vinyl chloride.

To this end, the invention relates to a process for the aqueous suspension polymerization of vinyl chloride with the use of dialkyl peroxydicarbonates with short alkyl chains, characterized in that the dialkyl peroxydicarbonate is used in the form of a solution in a dialkyl alkanedicarboxylate which is liquid and insoluble in water.

The solution of dialkyl peroxydicarbonate with short alkyl chains which is used according to the process of the present invention consists essentially of dialkyl peroxydicarbonate and of solvent (dialkyl alkanedicarboxylate). It is therefore free from other polymerization ingredients such as, for example, monomer.

Dialkyl alkanedicarboxylate (hereinafter referred to briefly as "ester") which is liquid and insoluble in water is intended to denote the esters which are liquid and insoluble in water in normal conditions, that is to say at ambient temperature and at atmospheric pressure. Insoluble in water is intended more particularly to mean a solubility in water at ambient temperature which is lower than 0.5 g/l. The solubility in water of the esters used as solvent for the peroxydicarbonate in the process of the invention preferably does not exceed 0.3 g/l.

The esters which are liquid and insoluble in water and used in the process of the invention generally have boiling temperatures (in normal conditions) which are appreciably higher than 100° C. In most cases they are higher than 150° C.

By way of examples of esters that can be applied there may be mentioned the liquid and water-insoluble esters as defined above which are derived from $C_4$–$C_{10}$ alkanedicarboxylic acids and from $C_2$–$C_{12}$ alkanols (linear or branched saturated aliphatic alcohols). Examples of these that may be mentioned are diethyl and dibutyl butanedicarboxylates (succinates), diethyl, dipropyl, dibutyl, diisobutyl and diethylhexyl hexanedicarboxylates (adipates), diethyl and dibutyl octanedicarboxylates (suberates) and dibutyl, diethylbutyl and diethylhexyl decanedicarboxylates (sebacates).

Esters which are well-suited for carrying out the process of the invention are the alkanedicarboxylates derived from $C_4$–$C_8$ alkanedicarboxylic acids and from $C_6$–$C_{10}$ alkanols. Esters which are very particularly preferred are chosen from hexanedicarboxylates (adipates) derived from adipic acid and from $C_6$–$C_{10}$ alkanols. An ester which is very particularly preferred in the process of the invention is diethylhexyl adipate.

The concentration of dialkyl peroxydicarbonate in the solutions used in the polymerization process according to the invention is generally from approximately 15 to 40% by weight. The use of dilute peroxydicarbonate solutions, for example of solutions containing approximately 10% by weight (or less) of dialkyl peroxydicarbonate, introduces the risk of resulting in vinyl chloride polymers whose glass transition temperature, and hence heat resistance, is reduced. In general, approximately 40% by weight is not exceeded because a concentration that is too high reduces the accuracy of the measurement when the reactor is fed with initiator. Good results are obtained with solutions in which the dialkyl peroxydicarbonate concentration is from approximately 25 to 35% by weight.

The solutions of dialkyl peroxydicarbonates with short alkyl chains that are used in the polymerization process according to the invention may be stored without risk at low temperature (below 10° C.) and this may be done for many hours without appreciable loss of activity. They can consequently be prepared in advance in a sufficient quantity to feed a number of polymerization reactors or else to feed a number of polymerization cycles in the same reactor.

For the purpose of the present invention, dialkyl peroxydicarbonates with short alkyl chains are intended to denote the peroxydicarbonates in which the alkyl radicals contain 2 or 3 carbon atoms and represent ethyl, propyl or isopropyl radicals, more particularly the ethyl and isopropyl radicals. A peroxydicarbonate which is very particularly preferred is diethyl peroxydicarbonate.

According to a particularly preferred embodiment of the process of the invention a diethyl or diisopropyl peroxydicarbonate is hence used in the form of a solution in a hexanedicarboxylate (adipate) derived from adipic acid and from a $C_6$–$C_{10}$ alkanol.

It is to be understood that, besides the dialkyl peroxydicarbonates with short alkyl chains, other conventional initiators may be used conjointly in the polymerization process of the invention. As examples of such other initiators there may be mentioned dilauroyl and dibenzoyl peroxides, azo compounds or dialkyl peroxydicarbonates with long alkyl chains, such as dicetyl peroxydicarbonate. Nevertheless, it is preferred to initiate the polymerization exclusively with the use of dialkyl peroxydicarbonates with short alkyl chains. In contrast to the other abovementioned peroxides, these have the advantage that their residues or excesses that may be present in polymerization mixture at the end of the polymerization cycle (and that could affect the thermal stability of the vinyl chloride polymers resulting from the process) are easily destroyed simply by alkalifying the mixture at the end of the polymerization cycle.

It is also to be understood that the dialkyl peroxydicarbonates in organic solution can be introduced, wholly or partially, after the beginning of the polymerization (with a delay). The delayed use of a portion of the dialkyl peroxydicarbonate with short alkyl chains is advantageous in order to improve the polymerization kinetics or else in order to produce resins with a low K value (which are produced at elevated temperature) exhibiting a good heat stability. The total quantity of initiator used generally ranges from approximately 0.15 to 0.90, and still more particularly from approximately 0.20 to 0.35 parts per thousand by weight approximately relative to the monomer(s) used.

Apart from the particular feature of the use of a dialkyl peroxydicarbonate with short alkyl chains ($C_2$ or $C_3$) in the form of a solution in an ester, the general polymerization conditions are those usually used for the noncontinuous polymerization of vinyl chloride in aqueous suspension.

For the purpose of the present invention vinyl chloride polymerization is intended to denote both the homopolymerization of vinyl chloride and its copolymerization with other ethylenically unsaturated monomers that can be polymerized by a radical route. Examples of conventional comonomers of vinyl chloride that can be used in the process of the invention and which may be mentioned are olefins, halogenated olefins, vinyl ethers, vinyl esters such as, for example, vinyl acetate, and acrylic esters, nitriles and amides. The comonomers are used in quantities which do not exceed 50 mol %, in most cases 35 mol %, of the mixture of comonomers used. The process according to the invention is highly suited for the homopolymerization of vinyl chloride.

Aqueous suspension polymerization is intended to mean the polymerization with the use of oil-soluble initiators, in this case especially dialkyl peroxydicarbonates with short alkyl chains, in the presence of dispersing agents such as, for example, water-soluble cellulose ethers, partially saponified polyvinyl acetates (also called polyvinyl alcohols) and mixtures thereof. Surface-active agents can also be used at the same time as the dispersing agents. The quantity of dispersing agent used generally varies between 0.7 and 2.0 parts per thousand by weight relative to the monomer(s).

The polymerization temperature is usually between approximately 40 and 80° C.

At the end of polymerization the vinyl chloride polymers produced according to the process of the invention are isolated in a conventional manner from their polymerization medium, generally after having been subjected to a purification from residual monomer(s).

The polymerization process of the invention allows an automation of the reactor feed. It results in an improvement in the reproducibility of the polymerization cycles. Furthermore, the use of the dialkyl peroxydicarbonates in the form of a solution in an ester according to the invention does not significantly affect the polymerization kinetics or the general properties (such as the K value, density and particle size) of the vinyl chloride polymers produced. In addition, when melt-processed, the latter provide shaped articles exhibiting a much smaller number of fisheyes.

The present invention also relates to an improved process for the two-stage manufacture of a solution of dialkyl peroxydicarbonate with short alkyl chains capable of being employed in (and particularly suited for) the aqueous suspension polymerization of vinyl chloride.

According to this process, in a first stage, a dialkyl peroxydicarbonate with short alkyl chains (as defined above) is manufactured by reacting appropriate quantities of alkyl haloformate with an inorganic peroxide in water in the presence of an inorganic salt in sufficient quantity to increase the density of the aqueous reaction medium and, in a second stage, the dialkyl peroxydicarbonate manufactured is isolated by extraction by means of a water-insoluble solvent, to produce a solution of dialkyl peroxydicarbonate in this solvent.

The inorganic salt is advantageously used in a sufficient quantity to bring the density of the aqueous reaction medium to a value of at least 1.05 and still more particularly to a value of at least 1.10. Furthermore, it is appropriate to adapt the quantity of inorganic salt so that it does not exceed the salt saturation concentration of the aqueous reaction medium.

The nature of the salt used in the stage of the manufacture of the dialkyl peroxydicarbonate is not particularly critical. In principle any inorganic salt that does not interfere with the reaction of formation of the dialkyl peroxydicarbonate, and which does not precipitate in the reaction conditions, is suitable. For example halides may be mentioned as nonlimiting examples of such salts, and in particular alkali and alkaline-earth metal chlorides. Alkali metal chlorides are preferably employed. According to a particularly advantageous embodiment, sodium chloride is employed.

The fact of carrying out the manufacture of the peroxydicarbonate in a densified aqueous medium results in the end in improving the efficiency of the isolation of the dialkyl peroxydicarbonate in solution.

The essential particular feature of the first stage is the use of an inorganic salt in sufficient quantity to increase the density of the aqueous reaction phase.

In most cases the reaction temperature is at a value situated between −10° C. and +10° C. The manufacture of the peroxydicarbonate is generally complete after a few minutes' reaction; the reaction period generally does not exceed 10 minutes and in most cases 5 minutes.

The alkyl haloformate is in most cases and advantageously a chloroformate. The inorganic peroxide is in most cases calcium or sodium peroxide or else aqueous hydrogen peroxide. In this latter case it is appropriate, in addition, to introduce a base, such as calcium hydroxide or sodium hydroxide, into the aqueous reaction medium.

It is particularly advantageous to use alkyl chloroformate with sodium peroxide or else hydrogen peroxide in the presence of sodium hydroxide as base (which leads to the formation of sodium chloride as byproduct), and, furthermore, to use sodium chloride as inorganic salt for densifying the aqueous phase. In this case the saline aqueous phase subsequently recovered (after isolation of the dialkyl peroxydicarbonate solution by extraction) can, without disadvantage, be recycled (optionally after dilution) to the manufacture of a new quantity of dialkyl peroxydicarbonate solution.

This procedure has the twin advantage of substantially reducing the usage of inorganic salt for densifying the aqueous phase and of reducing, or even eliminating, the environmental problems related to the removal of the saline aqueous phase after the manufacture of the dialkyl peroxydicarbonate.

The nature of the water-insoluble solvent employed in the second stage for the extraction of the dialkyl peroxydicarbonate is not particularly critical. A water-insoluble solvent is intended to denote a solvent which is insoluble in water at ambient temperature and atmospheric pressure and, more particularly, a solvent whose solubility in water in these conditions is lower than 0.5 g/l and still more particularly lower than 0.3 g/l.

By way of nonlimiting examples of solvents that can be employed for the extraction of the dialkyl peroxydicarbonate there may be mentioned the water-insoluble organic compounds chosen from the usual plasticizers for polyvinyl chloride. Nonlimiting examples of such solvents which may be mentioned are esters of aromatic polycarboxylic acids (like dibutyl or diethylhexyl phthalates), alkyl epoxycarboxylates (like octyl epoxystearate), epoxidized oils (like epoxidized soya oil) or the dialkyl alkanedicarboxylates the definition of which is given above in the context of the description of the dialkyl peroxydicarbonate solutions used in the aqueous suspension polymerization of vinyl chloride.

It is particularly advantageous to choose a solvent which furthermore has a relative density lower than 1 and preferably lower than 0.95.

Solvents that are particularly preferred are chosen from dialkyl alkanedicarboxylates derived from $C_4$–$C_8$ alkanedicarboxylic acids and from $C_6$–$C_{10}$ alkanols. Solvents that are very particularly preferred are chosen from the hexanedicarboxylates (adipates) derived from adipic acid and from $C_6$–$C_{10}$ alkanols. Excellent results are obtained with diethylhexyl adipate (boiling temperature at atmospheric pressure: 214° C., solubility in water at ambient temperature: <0.2 g/l, density: 0.922).

The quantity of solvent employed for the extraction is not critical. It is obvious that it will depend especially on the degree of solubility of the dialkyl peroxydicarbonate in the solvent chosen. This quantity will advantageously be such that the final concentration of the dialkyl peroxydicarbonate solution is from approximately 15 to approximately 40% by weight and still more particularly from 25 to 35% by weight.

The second stage of manufacture of the dialkyl peroxydicarbonate solutions, namely the isolation by extraction of the dialkyl peroxydicarbonate manufactured in the first stage, is performed in any known and appropriate manner.

The extraction solvent is advantageously added to the aqueous reaction mixture after the reaction of manufacture of the dialkyl peroxydicarbonate is finished, the phases are allowed to settle out and the supernatant organic phase is separated from the aqueous reaction phase in order to collect a pure peroxydicarbonate solution.

It is imperative to add the extraction solvent to the aqueous reaction mixture only after the end of the reaction of formation of the peroxydicarbonate. It has been found, in fact, that when the solvent is present from the beginning of the reaction, its presence has the effect of slowing the reaction down and of affecting the purity of the peroxydicarbonate solutions finally produced. In practice, therefore, the addition of the solvent will take place at the earliest approximately 5 minutes after the beginning of the reaction.

According to a very particularly preferred and advantageous embodiment, a solution of dialkyl peroxydicarbonate with short alkyl chains (such as diethyl, dipropyl or diisopropyl) containing from 15 to 40% by weight of dialkyl peroxydicarbonate is manufactured by using, in the first stage of the process of manufacture, sodium chloride as inorganic salt in order to increase the density of the aqueous phase and, in the second stage, of $C_6$–$C_{10}$-alkanol adipates, in particular diethylhexyl adipate, as extraction solvent for producing a solution of dialkyl peroxydicarbonate.

The invention also relates to a process for the manufacture of a solution of dialkyl peroxydicarbonate in which the alkyl radicals contain 2 or 3 carbon atoms according to which, in a first stage a dialkyl peroxydicarbonate in which the alkyl radicals contain 2 or 3 carbon atoms is manufactured by reacting, in water, appropriate quantities of alkyl haloformate with an inorganic peroxyde in the presence of an inorganic salt in sufficient quantity to increase the density of the aqueous reaction mixture and, in a second stage, the dialkyl peroxydicarbonate manufactured is isolated by extraction by means of a water-insoluble solvent, chosen from the water-insoluble organic compounds chosen from the usual plasticizers for polyvinyl chloride, in order to produce a solution of dialkyl peroxydicarbonate in this solvent.

The process of manufacture of dialkyl peroxydicarbonate solutions according to the invention provides solutions that are pure and stable in storage, in high yields. These solutions can be conveyed without danger and do not give rise to problems of deposits in conduits.

EXAMPLE 1

The example which follows is intended to illustrate the invention. It relates to the aqueous suspension homopolymerization of vinyl chloride with the use of diethyl peroxydicarbonate in solution containing approximately 30% by weight in diethylhexyl adipate. The peroxydicarbonate is manufactured from ethyl chloroformate, hydrogen peroxide and sodium hydroxide, before being extracted with diethylhexyl adipate.

Preparation of the Solution of Diethyl Peroxydicarbonate

Into a 1000-1 stirred reactor cooled below 10° C. are introduced 622 kg of an aqueous solution of sodium chloride containing 180 g/kg (that is 510 kg of demineralized water and 112 kg of NaCl), precooled to 5° C. 20.4 kg of ethyl chloroformate and 8.5 kg of aqueous solution of hydrogen peroxide containing 350 g/kg are then introduced successively into the stirred aqueous solution, and finally, very slowly, 36.1 l of aqueous solution of sodium hydroxide containing 200 g/kg, so as to maintain the temperature below 10° C. The density of the aqueous reaction mixture rises to 1.11. 10 minutes after the end of the introduction of the NaOH solution 34.5 kg of diethylhexyl adipate are introduced, precooled to 5° C. After the reaction mixture has been kept stirred for 15 minutes while being cooled to 5° C., the stirring is stopped. The aqueous phase (dense phase) is then separated off after settling out and the organic phase is recovered. The solution of diethyl peroxydicarbonate in diethylhexyl adipate which is thus produced is stored at 5° C. with a view to its subsequent use. Its diethyl peroxydicarbonate content (determined by analysis) is 287 g/kg.

Vinyl Chloride Polymerization

Into a reactor with a capacity of 3.9 m$^3$, equipped with a stirrer and a jacket, are introduced at ambient temperature and with stirring (50 rev/min) 1869 kg of demineralized water, 0.801 kg of polyvinyl alcohol (degree of hydrolysis 72 mol %) and 0.534 kg of polyvinyl alcohol (degree of hydrolysis 55 mol %), and 1.793 kg of the initiator solution prepared as above (that is 0.515 kg of diethyl peroxydicarbonate). The reactor is closed, the stirring is stopped and the reactor is placed under partial vacuum (60 mm Hg absolute), which is maintained for 5 minutes. The stirrer is restarted (110 rev/min) and 1335 kg of vinyl chloride are then introduced. The mixture is heated to 53° C., after which cold water is circulated through the jacket. The instant when the polymerization mixture reaches 53° C. is considered to be the beginning of the polymerization (time=$t_0$). After 6 h of running (counted from $t_0$) the pressure in the reactor has dropped by 1.5 kg/cm$^2$. The polymerization is stopped by successively performing an introduction of 0.35 kg of ammonia, the degassing of the unconverted vinyl chloride and cooling. The polyvinyl chloride produced is isolated from the aqueous suspension in conventional manner. 1118 kg of PVC are collected, the K value of which (at 20° C. in cyclohexanone at a concentration of 5 g/l) is 71.0.

The table below summarizes the properties evaluated on the PVC produced: K value (at 20° C. in cyclohexanone at a concentration of 5 g/l), apparent density (AD), porosity (% absorption of diethylhexyl phthalate), particle size distribution and, finally, the number of fisheyes, expressed as points per dm$^2$ and evaluated on a film extruded starting with a mixture of 100 parts by weight of PVC and 40 parts of diethylhexyl phthalate.

EXAMPLE 2 (COMPARATIVE)

By way of comparison, the vinyl chloride polymerization was reproduced in the same conditions as in Example 1, except that the appropriate quantity of diethyl peroxydicarbonate was first synthesized in situ in the polymerization reactor by reacting, at ambient temperature and with stirring, 0.734 kg of ethyl chloroformate and 0.109 kg of hydrogen peroxide in the presence of the total quantity of water (alkalified by addition of 0.284 kg of sodium hydroxide) and of the total quantity of polyvinyl alcohols intended for the polymerization (cf. Example 1: i.e. 1860 kg of water and, in all, 1.335 kg of polyvinyl alcohols). At the end of "in situ" synthesis of the initiator the reactor is closed, the stirring is stopped and the reactor is placed under partial vacuum (60 mm Hg absolute) for 5 minutes and 1335 kg of vinyl chloride are introduced with stirring (110 rev/min). The heating and the polymerization are subsequently carried out as in Example 1. After 5 h 51 min the pressure in the reactor has dropped by 1.5 kg/cm$^2$ and the polymerization is stopped. 1092 kg of PVC are collected, the K value of which (measured in the same conditions) is 71.3.

The table below also summarizes the properties evaluated on the PVC produced according to comparative Example 2.

From the comparison of the results shown in the table it appears that the use of diethyl peroxydicarbonate in solution of diethylhexyl adipate (according to the invention) has no significant effect on the polymerization kinetics or on the general properties of the PVC produced. In addition, the film extruded by starting from the PVC produced according to the invention (Example 1) has a significantly reduced number of fisheyes by comparison with a film extruded by starting from PVC produced with the use of diethyl peroxydicarbonate produced "in situ" (comparative Example 2).

TABLE

| Example number | 1 | 2 |
|---|---|---|
| Total polymerization period, h min | 6.00 | 5.51 |
| K value | 71.0 | 71.3 |
| AD, kg/l | 0.484 | 0.486 |
| Porosity, % | 33.3 | 32.5 |
| Particle size distribution, g/kg | | |
| >250 µm | 4 | 5 |
| 177–250 µm | 57 | 72 |
| 125–177 µm | 461 | 507 |
| 88–125 µm | 422 | 369 |
| 63–88 µm | 54 | 46 |
| 45–63 µm | 2 | 1 |
| <45 µm | 0 | 0 |
| Number of fisheyes, pts/dm$^2$ | 8 | 44 |

What is claimed:

1. A process for manufacturing a solution of a dialkyl peroxydicarbonate in which alkyl radicals thereof contain 2 or 3 carbon atoms, comprising reacting, in water, alkyl haloformate, in which the alkyl radicals thereof contain 2 or 3 carbon atoms, with an inorganic peroxide to form the dialkyl peroxydicarbonate in an aqueous reaction mixture, adding an inorganic salt to the aqueous reaction mixture to increase the density of the aqueous reaction mixture; and extracting the formed dialkyl peroxydicarbonate with a water-insoluble solvent to produce the solution of dialkyl peroxydicarbonate, wherein the water-insoluble solvent is a plasticizer for polyvinyl chloride.

2. The process according to claim 1 wherein the water-insoluble solvent is selected from a group consisting of esters of aromatic polycarboxylic acids, alkyl epoxycarboxylates, epoxidized oils and dialkyl alkanedicarboxylates.

3. The process according to claim 1, wherein the increased density has a value of at least 1.05.

4. The process according to claim 1, wherein the inorganic salt is sodium chloride.

5. The process according to claim 1, wherein the dialkyl peroxydicarbonate is diethyl peroxydicarbonate or diisopropyl peroxydicarbonate.

6. The process according to claim 1 wherein the alkyl haloformate is a chloroformate.

7. The process according to claim 1 wherein the inorganic peroxide is hydrogen peroxide in the presence of sodium hydroxide or sodium peroxide.

8. The process according to claim 7 wherein the inorganic peroxide is hydrogen peroxide in the presence of sodium hydroxide.

9. A process for manufacturing a solution of a dialkyl peroxydicarbonate in which alkyl radicals thereof contain 2 or 3 carbon atoms, comprising reacting, in water, alkyl haloformate, in which the alkyl radicals thereof contain 2 or 3 carbon atoms, with an inorganic peroxide to form the dialkyl peroxydicarbonate in an aqueous reaction mixture, adding an inorganic salt to the aqueous reaction mixture to increase the density of the aqueous reaction mixture; and extracting the formed dialkyl peroxydicarbonate with a dialkyl alkanedicarboxylate derived from a $C_4$–$C_{10}$ alkanedicarboxylic acid and a $C_2$–$C_{12}$ alkanol, to produce the solution of dialkyl peroxydicarbonate.

10. The process according to claim 9, wherein the dialkyl alkanedicarboxylate is derived from a $C_4$–$C_8$ alkanedicarboxylic acid and a $C_6$–$C_{10}$ alkanol.

11. The process according to claim 10, wherein the dialkyl alkanedicarboxylate is a dialkyl hexanedicarboxylate (adipate) derived from adipic acid and a $C_6$–$C_{10}$ alkanol.

12. The process according to claim 11, wherein the dialkyl hexanedicarboxylate is diethylhexyl adipate.

13. The process according to claim 9, wherein the increased density has a value of at least 1.05.

14. The process according to claim 9, wherein the inorganic salt is sodium chloride.

15. The process according to claim 9, wherein the dialkyl peroxydicarbonate is diethyl peroxydicarbonate.

16. The process according to claim 9 wherein the alkyl haloformate is a chloroformate.

17. The process according to claim 9 wherein the inorganic peroxide is hydrogen peroxide in the presence of sodium hydroxide or sodium peroxide.

18. The process according to claim 17 wherein the inorganic peroxide is hydrogen peroxide in the presence of sodium hydroxide.

19. A process for manufacturing a solution of diethyl peroxydicarbonate, comprising reacting, in water, ethyl haloformate with an inorganic peroxide to form diethyl peroxydicarbonate in an aqueous reaction mixture, adding an inorganic salt to the aqueous reaction mixture to increase the density of the aqueous reaction mixture; and extracting the formed diethyl peroxydicarbonate with a water-insoluble solvent to produce the solution of diethyl peroxydicarbonate, wherein the water-insoluble solvent is a plasticizer for polyvinyl chloride.

* * * * *